United States Patent [19]
Clark et al.

[11] 3,948,266
[45] Apr. 6, 1976

[54] NEEDLELESS HYPODERMIC INJECTOR
[76] Inventors: Wesley D. Clark, 26870 Taaffe Road, Los Altos Hills, Calif. 94022; Keith E. Hollenbeck, 847 Tulane Court, Mountain View, Calif. 94040
[22] Filed: Oct. 25, 1974
[21] Appl. No.: 518,039

Related U.S. Application Data
[63] Continuation-in-part of Ser. No. 342,508, March 19, 1973, Pat. No. 3,853,125.

[52] U.S. Cl. ............................... 128/272; 128/173 H
[51] Int. Cl.² ........................................ A61M 5/30
[58] Field of Search ....... 128/173 H, 173 R, DIG. 5, 128/239, 2 F, 272, 215, 216

[56] References Cited
UNITED STATES PATENTS

| | | | |
|---|---|---|---|
| 2,645,338 | 7/1953 | Scherer | 128/173 H |
| 3,330,276 | 7/1967 | Gordon | 128/173 H |
| 3,330,277 | 7/1967 | Gabriels | 128/173 H |
| 3,369,708 | 2/1968 | Hein | 128/272 X |
| 3,527,212 | 9/1970 | Clark | 128/173 H |

FOREIGN PATENTS OR APPLICATIONS

| | | | |
|---|---|---|---|
| 880,516 | 11/1970 | Italy | 128/2 F |

*Primary Examiner*—Robert W. Michell
*Assistant Examiner*—Henry J. Recla
*Attorney, Agent, or Firm*—Lowhurst & Aine

[57] ABSTRACT

A needleless hypodermic injector ampule includes a main body forming a chamber which is at less than ambient pressure, a cannula extending from one wall of the body, and a rigid discharge portion contiguous with the body and having a bore extending therethrough, which bore is in fluid communication with the chamber and terminates in an orfice which is dimensioned for needleless injection. A method of needleless medicant injection with an ampule having a medicant chamber and a bore extending therefrom dimensioned for needleless injection includes the steps of evacuating the medicant chamber such that it is at less than ambient pressure, sealing the chamber from ambient pressure, thereafter exposing the chamber to a contained medicant to permit transfer of the medicant into the chamber, and then exposing the medicant in the chamber to a higher than ambient pressure to force it through the bore.

4 Claims, 3 Drawing Figures

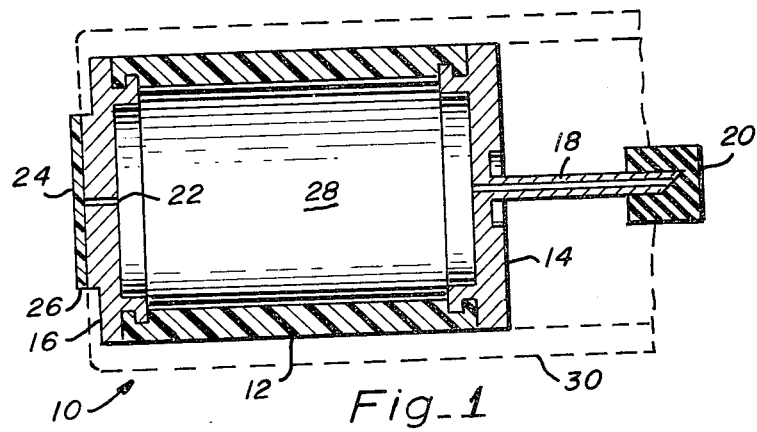
Fig_1
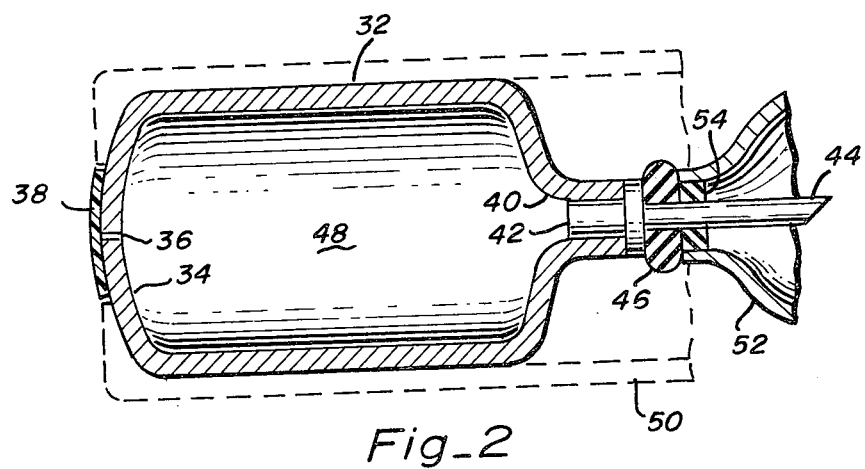
Fig_2
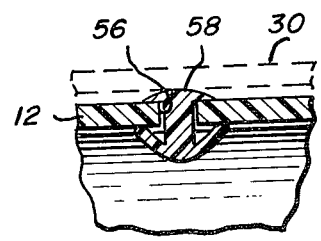
Fig_3

NEEDLELESS HYPODERMIC INJECTOR

The present application is a continuation-in-part application of parent application U.S. Ser. No. 342,508, filed Mar. 19, 1973 now U.S. Pat. No. 3,853,125, and entitled DISPOSABLE NEEDLELESS INJECTOR.

BACKGROUND OF THE INVENTION

1. Field of the Invention

This invention relates generally to hypodermic injection devices and more particularly to a needleless hypodermic injector ampule which can be charged with a medicant immediately prior to its use.

2. Prior Art

Application for U.S. Pat. Ser. No. 342,508, which is the parent application to this application, discusses some of the prior art pertaining to needleless hypodermic injection and some of the disadvantages associated therewith. That application discloses and claims a disposable needleless injector which employs a medicant containing ampule formed of a suitable material, such as stainless steel, which is inert with respect to the medicant contained therein. It can be readily appreciated that the use of stainless steel to form a medicant containing ampule is relatively expensive, particularly if the ampule is of the disposable type.

However, the use of relatively inexpensive materials results in other disadvantages. The major problem encountered in the use of inexpensive materials is the prolonged storage of medicants. That is, many of the inexpensive materials which are suitable for the fabrication of an ampule interact over extended periods of time with the majority of medicants which may be contained in such an ampule. Plastics are of this character. Other inexpensive materials are not suitable for the fabrication of ampules for one or more reasons. The U.S. Food and Drug Administration requires the prolonged storage of medicants in either glass or rubber containers. However, glass is fragile and, therefore, is not a desirable medicant container, particularly as an ampule in a needleless injector, since it must be able to withstand internal pressures during an injection. The yieldability of rubber makes its unsuitable, since it must be reinforced before it can be used under pressurized conditions which exist during a needleless injection with the device.

If it is feasible to fill an ampule immediately prior to its use, some of the relatively inexpensive materials are acceptable, since the medicant does not have an opportunity to interact with the containing material. Plastics and aluminum have all of the qualities which are desirable, such as rigidity, if the ampule is filled with the medicant immediately prior to its use.

It has been the practice in the past to supply a user with a large number of prefilled ampules, each containing a specified medicant. If a particular medicant is not used specifically in needleless injections, it may become stale and may have to be discarded after a period of time. On the other hand, if a medicant is used extensively for needleless injection and all of the prefilled ampules containing that medicant have been used, the user cannot refill such ampules from a larger supply. It can be appreciated, therefore, that a need exists for a medicant ampule for use in a needleless injector which can be filled immediately prior to its use quickly and easily by the user.

SUMMARY OF THE INVENTION

It is, therefore, an object of the present invention to provide a medicant ampule for needleless injectors which can be filled with a desired medicant immediately prior to its use quickly and easily by the user.

Another object of the present invention is to provide a method of needleless medicant injection with an ampule having a medicant chamber which can be filled with a desired medicant immediately prior to its use quickly and easily by the user.

A further object of the present invention is to provide a medicant ampule for needleless injectors which is formed of an inexpensive material.

Still another object of the present invention is to provide a medicant ampule for needleless injectors which is disposable.

Yet another object of the present invention is to provide a medicant ampule for needleless injectors which can be filled immediately prior to its use without the aid of other apparatus or articles.

Another object of the present invention is to provide a medicant ampule for needleless injectors which can be filled with any medicant which is desired by the user thereof, and such filling can be accomplished immediately prior to its use, if desired.

These and other objects of the present invention are attained by a medicant ampule for needleless injection which includes a main body forming a chamber which is at or can be reduced to less than ambient pressure, such that a medicant can be drawn into the chamber under the influence of the vacuum therein. The ampule may be supplied to the user with the medicant chamber at less than ambient pressure, or it may be provided with a sealable opening to permit the connection of a vacuum source to the chamber to reduce the pressure therein, thereby permitting the medicant to be drawn therein.

An important advantage of the present invention is that the ampule can be filled immediately prior to its use quickly and easily by the user thereof. Accordingly, the ampule can be formed of a material which is relatively inexpensive. Furthermore, the invention obviates the need for storing medicants in such an ampule for long periods of time, thereby eliminating all of the above mentioned problems associated with such storage of medicants.

The invention also includes the method of needleless injection with an ampule having a medicant chamber and a bore extending therefrom which is dimensioned for needleless injection. The method includes the steps of evacuating the medicant chamber such that it is at less than ambient pressure, exposing the chamber to a contained medicant which is approximately at ambient pressure to permit transfer of such medicant into the chamber, and then exposing the medicant in the chamber to a higher than ambient pressure to force it through the bore.

The invention, however, as well as other objects, features and advantages thereof will be more fully realized and understood from the following detailed description, when taken in conjunction with the accompanying drawing, wherein:

BRIEF DESCRIPTION OF THE DRAWING

FIG. 1 is a sectional view of a medicant ampule for needleless injectors which is constructed in accordance with the principles of the present invention.

FIG. 2 is a sectional view of an alternate embodiment of a needleless injector ampule of the present invention.

FIG. 3 is a broken away, sectional view of still another embodiment of the present invention.

DETAILED DESCRIPTION OF THE PREFERRED EMBODIMENTS

The term "dimensioned for needleless injection," as used herein and in the appended claims in connection with a discharge bore and orifice, means an orifice having a diameter and a bore having a diameter and length combination which provides an acceptable subcutaneous-intramuscular injection.

With reference to FIG. 1, there is shown a medicant ampule for needleless injectors which is constructed in accordance with the principles of the present invention. The ampule includes a main body, generally designated with the reference numeral 10, which is formed of a generally cylindrical side wall 12 and a pair of end walls 14 and 16. The side wall 12 is preferably formed of a plastic material which can be molded around the internal annular flanges of the end walls 14 and 16. It is to be understood, of course, that the side wall 12 can be constructed of any suitable material which will not interact with a medicant which may be contained within the ampule over a relatively short period of time. End walls 14 and 16 are preferrably formed of a metallic material. A cannula 18 extends from the end wall and is provided with a sharply pointed end for puncturingly engaging a weakened plug 20 of rubber, for example.

End wall 16 forms a rigid discharge portion of the body 10 and includes a bore 22 which is dimensioned for needleless injection and terminates in a discharge orifice. A seal 24 which may be formed of plastic, a wax layer, or a varnish layer is provided with an adhesive backing 26 and is mounted over the discharge orifice. The plug 20 and seal 24 effectively seal the main body 10 to provide a chamber 28. During manufacture of the device, the chamber 28 is evacuated, such that it is at less than ambient pressure.

When it is desired to fill the ampule illustrated in FIG. 1 with a medicant, the plub 20 is placed against the stopper of a vial containing the desired medicant. By pressing on the wall 16, the sharply pointed end of the cannula 18 pierces the plug 20 and stopper of the medicant vial, such that the passage through the cannula 18 is placed in fluid communication with the medicant contained in the vial. Under the influence of the vacuum in the chamber 28, the medicant is drawn into the ampule. When the chamber 28 has filled sufficiently with the medicant, the cannula 18 is withdrawn from the medicant vial and placed into an injector device, such as that disclosed in the parent application. Such an injector device is partially illustrated in FIG. 1 by the dotted line outline designated with the reference numeral 30. As taught in the parent application, the injector device 30 includes a container of pressurized gas is pierced by the cannula 18 during the injection to pressure the medicant in the chamber 28 to provide a high pressure injection stream through the bore 22. Of course, the seal 24 is removed and the device is properly placed on one's body prior to such pressurization.

An alternate embodiment of the present invention is illustrated in FIG. 2 wherein the ampule is formed of a main body 32 which is preferably constructed of spun aluminum. An end wall 34 of the body 32 is provided with a bore 36 which is dimensioned for needleless injection. An adhesive backed seal 38 is mounted over the discharge orifice of the bore 36. Main body 32 is provided with an opening 40 at one end thereof which is disposed for receiving an enlarged portion 42 of a cannula 44. The enlarged portion 42 is pressed into the opening 40, such that the opening 40 is sealed. A plug 46 is mounted on the sharply pointed end of the cannula 44 to seal the passage therethrough. Chamber 48 within the main body 32 is evacuated during manufacture of the ampule and is sealed by the seal 38 and the plug 46. The plug 46 is illustrated in FIG. 2 in its position after a medicant has been drawn into the chamber 48. It can be appreciated, however, that prior to such filling the plug 46 will have the same position with respect to the cannula 44 as the plug 20 has with respect to the cannula 18 is FIG. 1. The chamber 48 is filled in a like manner as the chamber 28 and as described above.

A portion of an injector device for receiving the ampule is shown in dotted line outline and designated with the reference numeral 50. When an injection is to be made, the seal 38 is removed and the ampule is placed into the device 50 in which is also placed a container 52 of pressurized gas. When an injection is being made, the cannula pierces a stopper 54 of the container 52, thereby placing the medicant in the chamber 48 under pressure.

If it is desirable to supply medicant ampules to a user without a partial vacuum, a hole 56 may be provided in a wall of the ampule, such as is illustrated in FIG. 3. The ampule can be filled by the user by connecting a vacuum source (not shown) to the opening 56 to draw medicant from a vial into the chamber. When the chamber has been filled, the opening 56 is closed by means of a flexible plug 58.

It can be appreciated that the invention can be practiced with devices other than the above described embodiments. More particularly, the invention can be practiced with any device which includes a medicant chamber and a bore extending therefrom which is dimensioned for needleless injection by evacuating the medicant chamber such that it is at less than ambient pressure, sealing the chamber from ambient pressure, thereafter exposing the chamber to a medicant which is approximately at ambient pressure to permit transfer of the medicant into the chamber, and then exposing the medicant in the chamber to a higher than ambient pressure to force it through the bore.

The invention claimed is:

1. An ampule for receiving and temporarily holding a medicant, comprising
    a. a main body forming a chamber, the interior of which is at less than ambient pressure,
    b. a cannula extending from one wall of said body and in fluid communication with the interior of said chamber,
    c. a rigid discharge portion contiguous with said body and having a bore extending therethrough which is in fluid communication with said chamber and is dimensioned for needleless injection,
    d. a puncturable seal mounted over the open end of said cannula, and
    e. a seal mounted over the open end of said bore.

2. The ampule of claim 1, wherein said main body is formed of a plastic material.

3. The ampule of claim 1, wherein said main body is formed of spun aluminum.

4. An ampule for receiving and temporarily holding a medicant, comprising
   a. a main body forming a chamber, and
   b. a cannula extending from said body and in fluid communication with the interior of said chamber, a wall of said body having a bore extending therethrough which is in fluid communication with said chamber and is dimensioned for needleless injection, one wall of said body having a sealable opening disposed for connection to a vacuum source, such that a medicant can be drawn into said chamber through said cannula under the influence of a vacuum at said opening.

* * * * *